United States Patent
Choulot et al.

(10) Patent No.: US 9,084,736 B2
(45) Date of Patent: Jul. 21, 2015

(54) **EXTRACT OF *LENTINUS* FOR ITS ACTION ON CELLULITE AND ACCUMULATIONS OF FAT**

(75) Inventors: Jean-Christophe Choulot, Rambouillet (FR); Patrick Ales, Paris (FR)

(73) Assignee: Caster, Paris (FR)

( * ) Notice: Subject to any disclaimer, the term of this patent is extended or adjusted under 35 U.S.C. 154(b) by 569 days.

(21) Appl. No.: 12/692,175

(22) Filed: Jan. 22, 2010

(65) Prior Publication Data

US 2010/0184721 A1 Jul. 22, 2010

(30) Foreign Application Priority Data

Jan. 22, 2009 (FR) ...................................... 09 50392

(51) Int. Cl.
| | |
|---|---|
| *A61K 8/73* | (2006.01) |
| *A61K 8/60* | (2006.01) |
| *A61K 8/96* | (2006.01) |
| *A61Q 19/06* | (2006.01) |
| *A61K 8/02* | (2006.01) |
| *A61K 8/97* | (2006.01) |

(52) U.S. Cl.
CPC .................. *A61K 8/73* (2013.01); *A61K 8/0229* (2013.01); *A61K 8/60* (2013.01); *A61K 8/975* (2013.01); *A61Q 19/06* (2013.01)

(58) Field of Classification Search
CPC ........... A61K 8/73; A61K 8/60; A61K 8/975; A61Q 19/06
See application file for complete search history.

(56) References Cited

U.S. PATENT DOCUMENTS

| | | | | |
|---|---|---|---|---|
| 6,585,974 | B1 * | 7/2003 | Fujimura et al. | 424/195.15 |
| 2003/0086949 | A1 * | 5/2003 | Perrier et al. | 424/401 |
| 2009/0270343 | A1 * | 10/2009 | Ales et al. | 514/54 |

FOREIGN PATENT DOCUMENTS

| | | |
|---|---|---|
| EP | 2 008 662 | 12/2008 |
| EP | 2 017 290 | 1/2009 |
| FR | 2 776 184 | 9/1999 |
| FR | 2 829 389 | 3/2003 |
| FR | 2 908 771 | 11/2006 |
| FR | 2 824 334 | 11/2008 |
| FR | 2 918 988 | 1/2009 |
| WO | WO 2006/041526 | 4/2006 |

OTHER PUBLICATIONS

Definition of treat, Merriam-Webster Dictionary, http://www.merriam-webster.com/dictionary/treat, accessed online on May 15, 2012.*
Fermiskin product webpage, Silab.fr, Internet Archive Wayback Machine dated Dec. 28, 2008, http://web.archive.org, accessed online on Dec. 17, 2012.*
machine translation of EP 2017290, European Patent Office, http://translationportal.epo.org, accessed online on Dec. 17, 2012.*
Hexsel et al., Dermatol. Surg., 2005, 31(7 Part 2), p. 866-872.*
Kim et al., International Journal of Dermatology, 2006, 45, p. 698-701.*
Brunet et al., "Akt promotes cell survival by phosphorylating and inhibiting a forkhead transcripton factor," *Cell*, 96:857-68, 1999.
Cheng HL et al., "Developmental defects and p53 hyperacetylation in Sir2 homolog (SIRT1)-deficient mice," *Proc. Natl. Acad. Sci. USA*, 2003.
Cohen et al., "Calorie restriction promotes mammalian cell survival by inducing the SIRT1 deacetylase," *Science*, 305(5682):390-392, 2004.
Dal Farra C. et al., "Sirt1, the human homologue to sirt2 is expressed in human skin and in cultured keratinocytes, fibroblasts and HaCaT cells; and its level is closely related to stress and aging," *J. Cosmetic Sci.*, 57:187-188, 2006.
HS Ghosh, "The anti-aging, metabolism potential of SIRT1," *Current Opinion in Investigational Drugs*, 9:1095-1102, 2008.
Jeong et al., "SIRT1 promotes DNA repair activity and deacetylation of Ku70," *Mol. Med.*, 39:8-13, 2007.
Langley et al., "Human SIR2 deacetylates p53 and antagonizes PML/p53-induced cellular senescence," *EMBO J.*, 2002.
Michishita et al., "Evolutionarily conserved and nonconserved cellular localizations and functions of human SIRT proteins," *Mol. Biol. Cell*, 16(10):4623-35, 2005.
Picard et al., "Sirt1 promotes fat mobilization in white adipocytes by repressing PPAR-γ," *Nature*, 429:771-76, 2004.
Porcu M. and Chiargui A., "The emerging therapeutic potential of sirtuin-interacting drugs: from cell death to lifespan extension" *Trends Pharmacol. Sci.*, 26(2):94-103, 2005.
Qiao et al., "SIRT1 regulates adiponectin gene expression through Foxo1-C/enhancer-binding protein alpha transcriptional complex," *J. Mol. Chem.*, 281(52):39915-24, 2006.
Rasouri et al., "SIRT1/PGC-1: a neuroprotective axisr?" *Medecine/Sciences*, 23:840-844, 2007. (French publication with English summary).
Sommer et al., "DeltaNp63alpha overexpression induces downregulation of Sirt1 and an accelerated aging phenotype in the mouse," *Cell Cycle*, 5(17):2005-2001, 2006.

* cited by examiner

*Primary Examiner* — Jonathan S Lau
(74) *Attorney, Agent, or Firm* — Norton Rose Fulbright US LLP (57) ABSTRACT

The present invention relates to the use of an extract of *Lentinus*, as well as the pharmaceutical composition that contains it, within the scope of combating cellulite and subcutaneous accumulations of fat.

10 Claims, 6 Drawing Sheets

Test

SIRT-1

EXTRACT OF *LENTINUS* FOR ITS ACTION ON CELLULITE AND ACCUMULATIONS OF FAT

BACKGROUND OF THE INVENTION

1. Field of the Invention

The present invention relates to the use of an extract of *Lentinus* as well as the pharmaceutical composition that contains it, within the scope of combating cellulite and subcutaneous accumulations of fat.

2. Description of Related Art

The sirtuins are nuclear enzymes belonging to the family of $NAD^+$-dependent deacetylases that occur in practically all organisms, from bacteria to humans.

These proteins, called "silent information regulators", exert their enzymatic activity on histones, but also on transcription regulators, and thus modulate their activity.

The sirtuins are in fact capable of deacetylating the histones on which the DNA is packed, making it less sensitive to UV and to DNases.

To date, seven sirtuins, called SIRT1 to SIRT7, have been identified in humans. Of these seven sirtuins, there is particular interest in SIRT1, which among other things is involved in skin aging (Dal Farra C. et al., *Sirt1, the human homologue to sirt2, is expressed in human skin and in cultured keratinocytes, fibroblasts and HaCaT cells; and its level is closely related to stress and aging, J. Cosmetic Scien.*, 2006, 57:187-188).

The activity of SIRT-1 deacetylase leads to inhibition of transcription of the genes involved, or "gene silencing". By this mechanism, SIRT-1 takes part in the regulation of protein p53, a transcription factor involved in the apoptotic cellular pathways, which is acetylated and activated during cellular stress or DNA damage. Thus, SIRT-1 can induce deacetylation of protein p53, i.e. its inactivation, and block its transcription, thus permitting prolongation of cellular longevity (Cheng H L et al. Proc Natl Acad Sci USA. 2003).

All of the bibliographical data clearly indicate that SIRT1 is involved in the ageing process (Porcu M. and Chiarugi A., Trends Pharmacol Sci, 2005; Langley E et al., EMBO J. 2002; H S Ghosh, Current Opinion in Investigational Drugs 2008 9:1095-1102; David Sidransky et al., Cell Cycle 5:17, 2005-2011, 1 Sep. 2006).

Increased expression of SIRT1 in young cells thus contributes, by deacetylation of protein p53 and of histones, to promotion of cellular longevity. However, expression of the protein SIRT1 decreases with age. It has in fact been shown that human fibroblasts aged by successive replicative passages display reduced endogenous expression of the protein SIRT-1 (Michishita et al., Mol Biol Cell. 2005 October; 16(10):4623-35).

In centenarians, the overexpression of certain genes (such as IL10) or of particular proteins such as the sirtuins might explain their longevity.

SIRT1 is therefore regarded as a longevity protein which:
promotes cell survival and participates in the natural DNA defence system by deacetylating the histones on which the DNA is packaged;
inhibits apoptosis by deacetylating the "DNA repair factor" protein Ku70, which permits this protein to sequester in the cytoplasm and inactivate the factor Bax, which is known to promote apoptosis (Brunet A et al., Cell. 1999; 96: 857-68; Jeong J et al., Mol Med. 2007; 39: 8-13);
deacetylates the nuclear protein p53, which is also involved in the induction of apoptosis.

The protein SIRT1 also acts at the level of the mitochondria, detoxifying the organism by removing free radicals. In fact, a signalling pathway was recently demonstrated involving the cofactor PGC-1, a key protein in biogenesis and mitochondrial function, and SIRT1 whose activation leads to an improvement in the functioning of the mitochondria (Johan Auwerx et al., MEDECINE/SCIENCES 2007; 23; 840-4).

The protein SIRT1 also possesses the capacity to intervene, at cellular level, in the mechanism that controls the accumulation of fat reserves.

Caloric restriction increases, on the one hand, the expression of SIRT1 in a large range of tissues and this alters the balance in favour of cell survival (David A. Sinclair et al., Science 16 Jul. 2004:Vol. 305. No. 5682, pp. 390-392). On the other hand, when the cell is deprived of nourishment, SIRT1 lowers the activity of another molecule, the nuclear receptor PPAR-gamma, which plays a role in the accumulation of fats (Picard F et al. Nature 2004; 429:771-76).

It is now known that SIRT 1 is identified as a mediator of adipogenesis by its action on lipolysis by inhibition of phosphodiesterase-4. Thus, at adipocyte level, SIRT 1 inhibits adipogenesis and increases lipolysis (Qiao L. et al. J. Mol. Chem. 2006 Dec. 29; 281 (52): 39915-24.). As the concentrations of SIRT1 decrease with age in mammals, this might explain why we put on weight as we get older.

The skin is the organ that provides a covering for the entire surface of the body, and is constituted of three superposed, separate compartments: the epidermis (the covering epithelium), the dermis (supporting connective tissue) and the hypodermis. The epidermis is a stratified epithelium that constitutes the external structure of the skin and provides its protective function. The dermis is a supporting tissue that participates in the strength, elasticity and especially the tonicity of the skin and/or of the mucosae. Underneath the dermis there is a layer of adipose tissues: the hypodermis.

The hypodermis is constituted of a layer of white adipose tissue arranged in lobules attached to the lower part of the dermis by rows of collagen fibres and elastic fibres. It is constituted of the large vacuolized cells, the adipocytes, filled almost entirely with triglycerides. These cells can change quickly in volume, during weight loss or weight gain, and can measure from 40 to 120 µm in diameter, which corresponds to a 27-fold change in volume.

The subcutaneous adipose tissue constitutes the body's largest energy reservoir. It is able to store lipids in the form of triglycerides by a process of lipogenesis and then release them in the form of fatty acids and glycerol by a process of lipolysis. It is the equilibrium between these two metabolic pathways that determines adiposity. The body's lipid reserves are constantly being renewed and are closely related to food intake and the energy needs of the body.

If an imbalance develops in the body between the processes of lipogenesis and lipolysis, the volume and the number of adipocytes may increase; this is called adipocyte hypertrophy and hyperplasia. The excessive development of the adipose mass may then be reflected in changes in the skin's appearance, or may even progress to excessive weight of the individual, and possibly obesity.

Cellulite, which is considered to be unsightly, corresponds to hypertrophy of the adipose cells through excess of triglycerides and hyperviscosity of the ground substance (by polymerization of polysaccharides). These changes interfere with cellular exchanges and the mobility of the connective fibres (collagen, elastin and reticulin), which is reflected in water retention, slowing of the venous and lymphatic circulation and loss of flexibility of the skin. The accentuation of adipose tissue is localized, especially in women, at the hips, thighs, buttocks, knees and forearms. The skin takes on a padded and dimpled appearance and at the most advanced stage the "orange-peel" appearance, which is characterized by a succession of depressions caused by excessive stretching of the connective tissue framework and drawing of the epidermis towards the deep tissues.

Nowadays, much research effort is directed at finding an effective means of combating cellulite and excess fat in general. Numerous methods have been employed, for example certain medical-surgical techniques such as lipoplasty, lymphatic drainage, mesotherapy, techniques of ionophoresis etc. However, although these techniques are effective, they are severe and restricting.

There is a need for a gentle, non-invasive means of acting on the mechanisms of formation of excess subcutaneous fat and cellulite.

Action on fatty acid metabolism by cosmetic and pharmaceutical actives so as to prevent the appearance of cellulite, for example by promoting lipolysis or else by inhibiting lipogenesis, i.e. decreasing the formation of triglycerides, has been considered.

However, there is still a need for compounds that make it possible to act on the actual formation and storage of excess subcutaneous fat.

SUMMARY OF THE INVENTION

The applicant discovered that extracts of *Lentinus* permit activation of the expression of the protein SIRT1 in keratinocytes, which constitutes the object of the invention.

Thus, the use of activators of expression of the protein SIRT1 is envisaged as a means of prevention or of local treatment of metabolic disorders associated with the presence of cellulite and accumulations of subcutaneous fat.

The applicant has thus developed a polysaccharide extract derived from fungus of the genus *Lentinus* for the treatment of cellulite and subcutaneous accumulations of fat.

The invention also relates to a pharmaceutical composition containing this extract.

Other objects will become clear on reading the description, the drawings and the examples given below.

DETAILED DESCRIPTION OF THE ILLUSTRATIVE EMBODIMENTS

*Lentinus edodes* (shiitake), an edible woodland mushroom from Japan, is known in many Asian countries (China, Korea, etc.) as one of the best mushrooms for its taste and its aroma. *Lentinus edodes* is in fact characterized by certain specific substances, for example guanosine 5'-monophosphate which produces a pleasant aroma and an aromatic substance, lenthionine.

Recently, the medicinal properties of the shiitake mushroom were investigated by Japanese researchers and antiviral, antibiotic, antitumour and hypolipidaemic effects were demonstrated.

A lentinan-rich aqueous extract of *Lentinus* is known for its antitumour properties from patent FR2776184. Patent FR2829389 describes a method of extraction of *Lentinus* comprising stages of enzymatic hydrolysis in order to obtain an extract capable of inhibiting the activity of certain metalloproteases, the MMPs and in particular MMP-1 and 2.

The polysaccharide extract derived from the *Lentinus* mushroom, according to the invention, is used for combating cellulite and subcutaneous accumulations of fat in a mammal, and more particularly a human.

This polysaccharide extract, by activating the expression of the protein SIRT1 in the cells of the skin, increases simultaneously the inhibition of adipogenesis and lipolysis.

The polysaccharide extract derived from mushroom of the genus *Lentinus*, according to the invention, preferably comprises monosaccharides, polysaccharides and, by weight, from 2 to 8% of trehalose, from 1 to 4% of glucose and from 30 to 60% of alditols relative to the total weight of the dry extract.

Preferably, said extract comprises, in addition to monosaccharides and polysaccharides, from 2 to 6% of trehalose, from 2 to 3% of glucose and from 45 to 55% of alditols by weight relative to the total weight of the dry extract. More preferably, said extract comprises, in addition to monosaccharides and polysaccharides, from 3 to 5% of trehalose, from 2 to 3% of glucose and from 45 to 50% of alditols by weight relative to the total weight of the dry extract.

Preferably, the alditols contained in said extract according to the invention comprise arabinitol and mannitol.

Preferably, the polysaccharide extract according to the invention is derived from the fungus *Lentinus edodes*.

Figure 1:
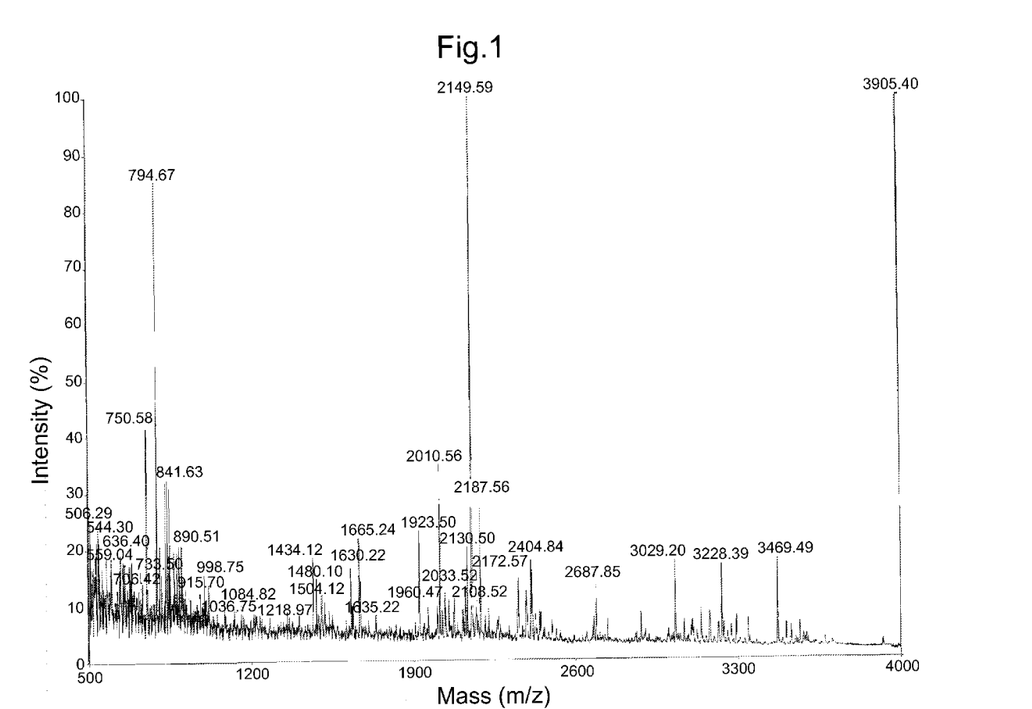
FIGS. 1 and 2 show an analysis by mass spectrometry (MALDI-TOF) of the polysaccharide extract obtained in Example 1. The molecular weights of the compounds shown range from 500 to 10 000 m/z (mass/charge).
Figure 2:
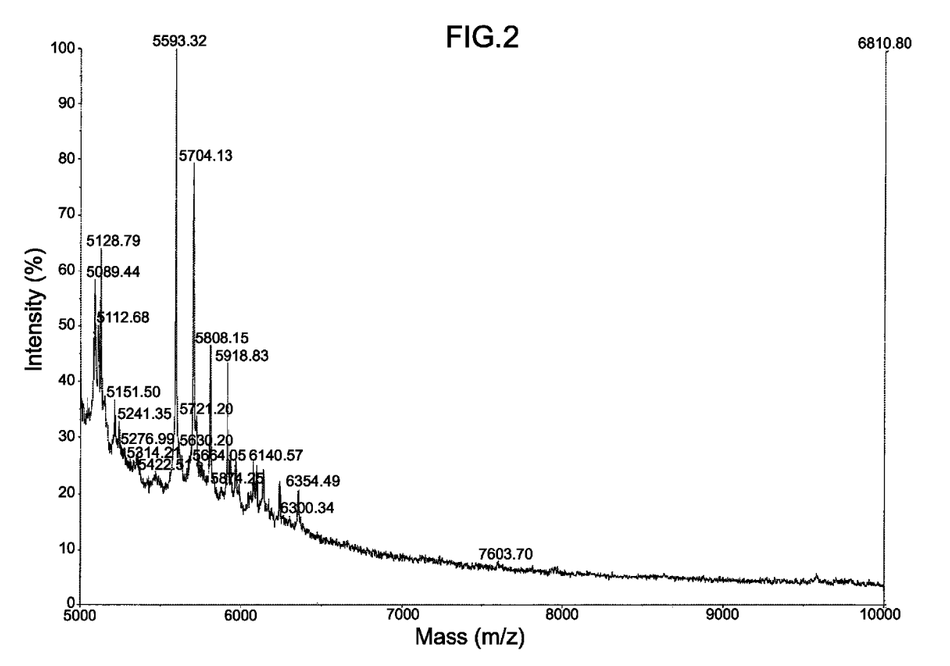

A particularly preferred polysaccharide extract according to the invention is defined by the mass spectrometry analyses in FIGS. 1 and 2.

The extract according to the invention can be in the form of powder.

The method of extraction of the extract according to the invention is described in patent application FR 2 918 988.

Briefly, one or more solid/liquid extractions are carried out, the liquid extract is precipitated with an organic solvent, centrifuged, filtered, then the precipitate is dried to obtain the polysaccharide extract.

In one embodiment of this method, the extraction or extractions are carried out with boiling water. Preferably, the organic solvent used is ethanol.

The extracts are obtained by the method described above from mushrooms of the genus *Lentinus*, which can be used dried. In general, the fresh mushrooms contain 85 to 95% water, and the air-dried mushrooms between 5 and 20% water. Preferably, the mushrooms are *Lentinus edodes*, otherwise called Lentinula edodes (Berk.), shii-take, shiitake, Cortinellus shiitake or Cortinellus edodes.

The polysaccharide extract according to the invention can be used cosmetically for combating cellulite and subcutaneous accumulations of fat in order to improve the aesthetic appearance of the body.

The invention also relates to pharmaceutical compositions comprising said polysaccharide extract, and optionally a physiologically acceptable excipient, for the treatment of humans or mammals suffering from cellulite or from excessive accumulations of subcutaneous fat.

The polysaccharide extract according to the invention can be incorporated or formulated in a polymeric vehicle or a delivery system for topical or local use.

Said compositions can be used for prevention or treatment.

The compositions according to the invention are applied on the skin or cutaneous surface of an individual. Depending on the method of administration, the compositions according to the invention can be in all the forms usually employed in cosmetics or as medication. Said compositions can in particular be formulated as ointments, creams, milks, gels.

EXAMPLES

The following examples illustrate the invention without limiting it in any way.

Example 1

Total Aqueous Extracts and Alcoholic Precipitate 1 kilogram of dried *Lentinus edodes* is ground in an Henri knife mill. The powder obtained is extracted with 3×10 liters of boiling distilled water. After stirring for 30 minutes at 90° C., it is filtered on a 50-liter Büchner filter on a layer of filter aid (Celite). It is concentrated to 5 liters in a Luwa thin-film evaporator, and is then lyophilized in a Serail lyophilizer. An aliquot from each aqueous extract is dissolved in distilled water and precipitated by adding 1.5 volume of 96° ethanol. It is left overnight in a coldroom and then centrifuged (IEC Centra 7R). It is dried in a desiccator under vacuum.

Example 2

Analysis of the Extract according to the Invention by Mass Spectrometry

The extract from Example 1 was analysed by mass spectrometry (MALDI-ToF). MALDI (Matrix Assisted Laser Desorption Ionization) is a method of ionization that makes it possible to analyse molecules whose molecular weight is greater than 1000 Da. The analyser coupled to the MALDI source is a time-of-flight (ToF) analyser, which is very suitable for pulsed ionization by laser desorption. Separation in a time-of-flight analyser is based on the fact that ions of different mass, accelerated to a uniform kinetic energy, have different velocities, and therefore a different time-of-flight for covering a given distance.

FIGS. 1 and 2 show a visualization of all of the compounds whose molecular weight is between 500 and 10 000 m/z.

Example 3

Characterization of the Extract from Example 1 by Chromatography

Figure 3:
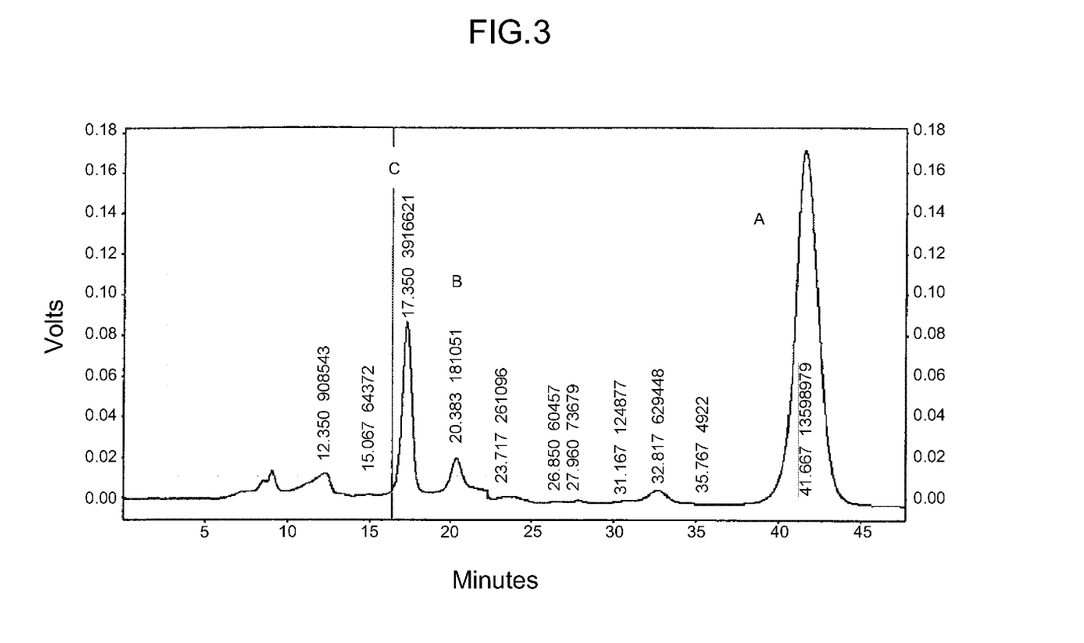
FIGS. 3 and 4 show chromatographic analyses of the polysaccharide extract obtained in Example 1. The analysis summarized in FIG. 3 was performed by ion-exchange liquid chromatography. That in FIG. 4 is size exclusion chromatography.

The raw extract from Example 1 was analysed by ion-exchange liquid chromatography on a CARBO-Sep column (CHO-682, Interchim), the unique selectivity of which makes it possible to separate mono- and disaccharides using only pure water as eluent. The chromatogram obtained (FIG. 3) shows the presence mainly of a small hydroxylated molecule (A) and, among others, two compounds which may correspond to a monosaccharide (B) and a disaccharide (C).

Figure 4:
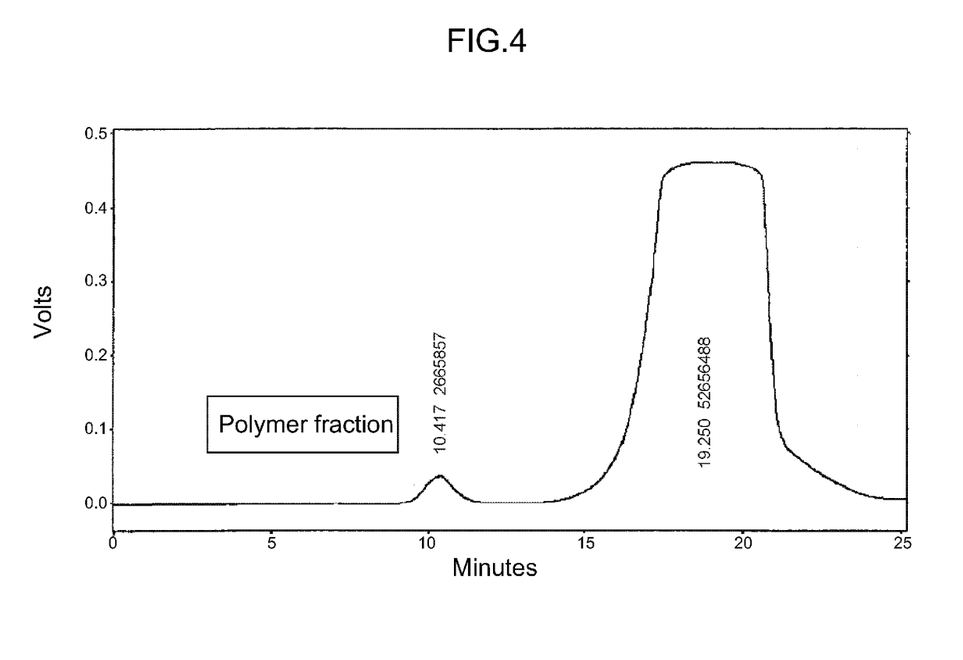

Secondly, the raw extract was analysed by size exclusion chromatography on the Shodex OHpak B-804 column (limit of exclusion: $4 \times 10^5$ kDalton). The chromatographic profile obtained shows that only 2% of the extract corresponds to polysaccharides (FIG. 4).

Example 4

Ultrafiltrations of the Extract from Example 1

Successive ultrafiltrations of the raw extract carried out on cellulose ultrafiltration membranes (Diaflo®-Amicon Co) characterized by three cut-off thresholds of 100 kDalton (kD), 10 kD and 1 kD resulted in 4 fractions being obtained (Lent. 100=MW>100 kD; Lent. 10=10 kD<MW<100 kD; Lent. 1=1 kD<MW<10 kD and Lent. UF=MW<1 kD), with the contents by weight shown below.

For each stage, washing with distilled water is regarded as completed when 10 volumes of liquid have passed through the membrane.

TABLE 1

| | Fractions | | | |
|---|---|---|---|---|
| | Lent. 100 | Lent. 10 | Lent. 1 | Lent. UF |
| Weight (mg) | 47 | 127 | 24 | 1874* |
| % | 2.4 | 6.5 | 1.2 | 89.9 |

*After correction of the water content

The fractions containing polysaccharides, Lent. 100 and Lent. 10 correspond to 8.9% (2.4%+6.5%) of the total weight of the active extract.

Total acid hydrolysis of 4 ultrafiltrates followed by analysis of the sugars by liquid chromatography was used for determining the nature of the carbohydrate components. The fraction Lent. UF, the main component of the extract (89.9%), contains apart from the monosaccharides (glucose, fucose, arabinose, mannose, xylose, arabinitol, mannitol) and disaccharides (trehalose), amino acids, vitamins and minerals.

The composition of sugars in fractions Lent. 1, Lent. 10 and Lent. 100 is presented in Table 2.

TABLE 2

Composition of neutral sugars in the fractions

| | Neutral sugars | | | | | | | |
|---|---|---|---|---|---|---|---|---|
| | Rhamnose | Fucose | Ribose | Arabinose | Xylose | Mannose | Galactose | Glucose |
| Lent 1 | 12.3 | 10.4 | 5.2 | 2 | 2.6 | 20 | 32.5 | 15 |
| Lent 10 | 12.6 | 5.3 | 15.4 | 1.3 | 4.5 | 21 | 13.8 | 26.1 |
| Lent 100 | 4 | 5.1 | 7.1 | 5.4 | 4.6 | 17.1 | 26.4 | 29.3 |

*calculation based on all of the neutral sugars identified

All of the results obtained following the various analyses of the active extract from Example 1 are presented in Table 3.

TABLE 3

| Constituents | (Lent. 100 + Lent. 10) of which polysaccharides | Fraction > 1 KD | Other constituents | Trehalose | Glucose | Other monosaccharides | Alditols |
|---|---|---|---|---|---|---|---|
| In % | 8.9 | 1.2 | 34.1 | 4 | 2.6 | 2.9 | 46.3 |

Example 5

Immunocytochemical Evaluation of the Expression of SIRT-1 in Human Keratinocytes Cloned human keratinocytes (HaCaT, German Cancer Research Center, Heidelberg, Germany) are cultivated on Lab-Tec slides (VWR International, Strasbourg, France) in DMEM medium (Lonza, Saint Beauzire, France) supplemented with 10% of fetal bovine serum (Lonza, Saint Beauzire, France) at 37° C. in a humidified atmosphere containing 5% $CO_2$.

The keratinocytes (8000 cells per well) are incubated with the extract of *Lentinus* from Example 1 to a final concentration of 0.1% in culture medium for 24 hours, untreated cells being used as controls.

After washing with PBS (phosphate-buffered saline) the keratinocytes are fixed with 4% paraformaldehyde (PFA). Next, the keratinocytes are permeabilized with Triton 0.1% (Sigma, Saint Quentin Fallavier, France).

Next, immunolabelling is carried out using, as primary antibody, a human anti-SIRT1 rabbit antibody (dilution 1:50) (Santa Cruz Biotechnology, California, USA) and, as secondary antibody, an anti-rabbit antibody coupled to Alexa Fluorine® 488 (dilution 1:50) (Invitrogen, Eragny-sur-Oise, France).

The photographs were taken using a fluorescence microscope (Nikon TE2000E) coupled to a digital camera (Nikon DXM1200F).

Figure 5A:
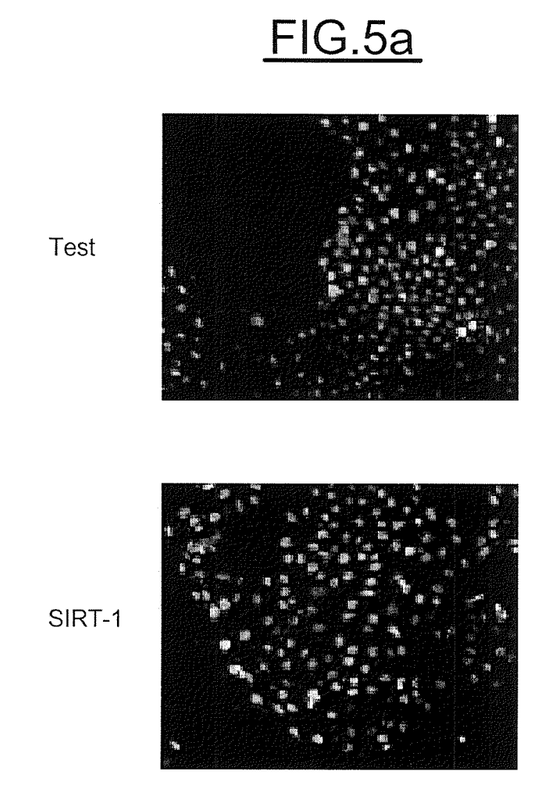
FIGS. 5a and 5b show, at different magnifications (FIG. 5a: magnification ×20 or FIG. 5b: magnification ×100), analyses of expression of the protein SIRT1 in keratinocytes in the presence or absence of an extract of *Lentinus* according to the invention.
Figure 5B:
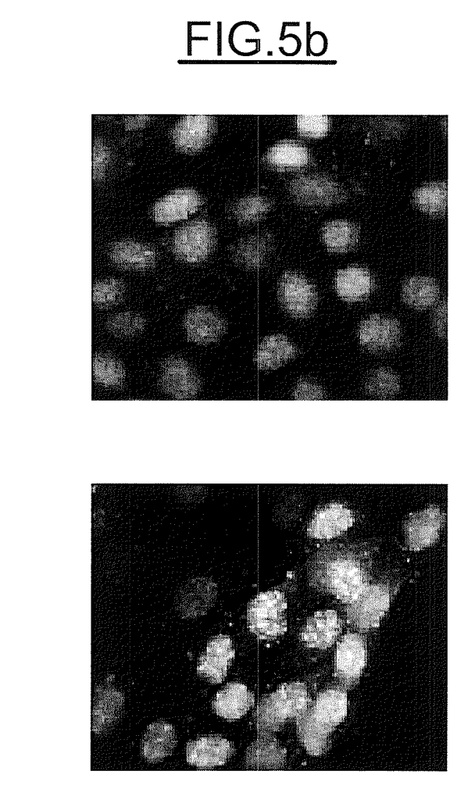

FIG. 5 clearly shows, at different magnifications, that the extract of *Lentinus* according to the invention causes expression of SIRT1 in keratinocytes, relative to the control.

Example 6

Semi-quantitative Analysis of the Protein SIRT1 by the Western Blot Technique Human keratinocytes (HaCaT) ($10^6$ cells) cultured in DMEM medium (Lonza, Saint Beauzire, France) supplemented with 10% of fetal bovine serum (Lonza, Saint Beauzire, France) at 37° C. in a humidified atmosphere containing 5% $CO_2$ are incubated as previously with the extract of *Lentinus* to a final concentration of 0.1% in culture medium for 24 hours, identical untreated cells being used as controls.

This is followed by cell lysis with 400 microliters of lysis buffer (Cell Lysis Buffer, Cell Signaling Technology, USA) supplemented with 1 mM of phenylmethylsulphonyl fluoride (PMSF), which is an irreversible protease inhibitor (Sigma, Saint Quentin Fallavier, France).

The proteins thus extracted are centrifuged at 10 000 rpm for 10 minutes at 4° C. and the supernatants obtained are stored at −80° C. before use.

The proteins present in 40 μg of the cell lysate (supernatant) are separated by polyacrylamide gel electrophoresis-SDS (12%) and then transferred to a PVDF (polyvinylidene fluoride) membrane (0.45 μm; Immobilon-FL, Millipore).

The nonspecific sites are blocked by incubation of the membrane with delipidated milk (Régilait, France) at 5% in TBST (Tris-Buffered Saline Tween-20) overnight at 4° C.

Then the membrane is incubated with a rabbit anti-SIRT1 human primary antibody (1/200) (Santa Cruz Biotechnology, California, USA) and then with an anti-rabbit secondary antibody (dilution 1:50 000) conjugated with peroxidase HRP (Daco, Trappes, France).

The membrane is then incubated with a chemoluminescence reagent (Immobilon Western HRP Substrate, Millipore), then development and quantification of the SIRT1 band are carried out on autoradiographic film using the Molecular Imager ChemiDoc XRS system (Bio-rad, France).

Figure 6:
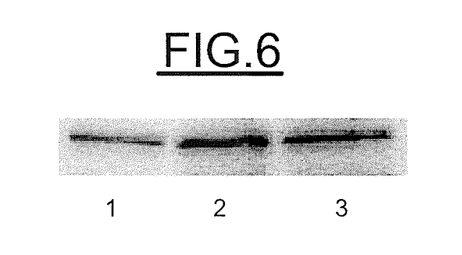
FIG. 6 is a semi-quantitative Western-blot analysis of the amount of protein SIRT1 present in keratinocytes treated with the polysaccharide extract according to the invention, or untreated. Track 1 shows the amount of protein SIRT-1 in a negative control, track 2 shows the amount of SIRT-1 in a positive control (resveratrol) and track 3 shows the amount of the protein SIRT-1 in keratinocytes treated with the polysaccharide extract of *Lentinus* according to the invention.

| | Name | Adj. Vol INT * $mm^2$ |
|---|---|---|
| Track 1 | Negative control | 549.08 |
| Track 2 | Positive control | 2477.04 |
| Track 3 | Extract of Lentinus according to the invention | 2303.44 |

These results clearly show a 500% increase in the amount of SIRT1 present in the keratinocytes treated with the extract of *Lentinus* from Example 1 (Track 3) relative to that quantified in the untreated cells (Track 1).

Example 7

Formulation of an Oil-in-water Cream (Expressed in %)

| | |
|---|---|
| Water | Q.S. 100 |
| Squalane | 5.00 |
| Petrolatum | 5.00 |
| Glycerol | 5.00 |
| Isodecyl Neopentanoate | 5.00 |
| Pentaerythrityl Tetraethylhexanoate | 5.00 |
| Cyclomethicone | 4.00 |
| Cetearyl Alcohol | 3.00 |
| Myristyl Myristate | 2.00 |
| Laureth-23 | 2.00 |
| Silica | 2.00 |
| Heptadecadienyl Furan | 0.1 to 10 |
| Beeswax | 1.00 |
| Sclerotium Gum | 1.00 |
| PEG-6 | 1.00 |
| Polyacrylamide | 0.80 |
| Glyceryl Stearate | 0.70 |
| Dimethiconol | 0.70 |
| Cetearyl Glucoside | 0.60 |
| C13-14 Isoparaffin | 0.40 |
| Citric acid | 0.14 |
| Laureth-7 | 0.10 |
| 4,5,7-Trihydroxyisoflavone | 0.01 to 10 |
| Caffeine | 0.1 to 10 |
| Extract of *Enteromorpha compressa* | 0.01 to 5 |
| Extract of *Garcinia cambogia* | 0.01 to 10 |
| Extract of *Ginkgo biloba* | 0.01 to 10 |
| *Lentinus edodes* | 0.02 to 5 |
| Extract of flowers of *Sophora japonica* | 0.01 to 20 |
| Hydrolysed soya protein | 0.01 to 10 |
| Preservative system | QS |
| Perfume | QS |

Example 8

Formulation of a Water-in-oil Cream (Expressed in %)

| | |
|---|---|
| Water | Q.S. 100 |
| Hydrogenated polyisobutene | 7.00 |
| Isocetyl Stearate | 7.00 |
| Cyclomethicone | 4.80 |
| Glycerol | 4.00 |
| Mineral Oil | 3.00 |
| Zinc oxide | 3.00 |
| Butylene Glycol | 2.00 |
| Isononyl Isononanoate | 2.00 |
| Beeswax | 2.00 |
| Cetyl Dimethicone Copolyol | 1.70 |
| Polyglyceryl-4 Isostearate | 1.65 |
| Hexyl laurate | 1.65 |
| Disodium tartrate | 1.60 |
| Sodium Chloride | 1.00 |
| PEG-6 | 1.00 |
| 4,5,7-Trihydroxyisoflavone | 0.01 to 10 |
| Retinyl palmitate | 0.01 to 10 |
| *Lentinus edodes* | 0.02 to 5 |
| Extract of *Enteromorpha compressa* | 0.01 to 5 |
| Extract of flowers of *Sophora japonica* | 0.01 to 20 |
| Extract of *Centella asiatica* | 0.01 to 5 |
| Hydrolysed soya protein | 0.01 to 10 |
| Preservative system | QS |
| Perfume | QS |

Example 9

Formulation of a Stick (Expressed in %)

| | |
|---|---|
| Castor Oil | Q.S. 100 |
| Oleyl Alcohol | 20.00 |
| Hydrogenated Palm Kernel Oil | 17.00 |
| Candelilla Wax | 11.00 |
| Polyglyceryl-3 Beeswax | 10.00 |
| Mineral Oil | 9.57 |
| Heptadecadienyl Furan | 0.1 to 10 |
| Shea butter | 2.00 |
| 4,5,7-Trihydroxyisoflavone | 0.01 to 10 |
| Quaternium-18 Hectorite | 1.10 |
| Titanium Dioxide | 1.00 |
| Tocopheryl Acetate | 0.50 |
| Propylene Carbonate | 0.33 |
| Perfume | QS |
| Retinol | 0.01 to 10 |
| *Lentinus edodes* | 0.02 to 5 |
| Extract of *Enteromorpha compressa* | 0.01 to 5 |
| Extract of flowers of *Sophora japonica* | 0.01 to 20 |
| Extract of *Centella asiatica* | 0.01 to 5 |
| Hydrolysed soya protein | 0.01 to 10 |

Example 10

Formulation of a Gel Cream (Expressed in %)

| | |
|---|---|
| Water | Q.S. 100 |
| Cyclomethicone | 5.40 |
| Octyl Palmitate | 5.00 |
| Hydrogenated Coco-glycerides | 3.00 |
| Arachidyl Behenyl Alcohol | 2.55 |
| Propylene Glycol | 2.50 |
| Isodecyl Neopentanoate | 2.00 |
| Glyceryl Stearate | 1.70 |
| Cetyl Alcohol | 1.30 |
| Stearic acid | 1.00 |
| PEG-6 | 1.00 |
| Beeswax | 0.40 |
| C13-14 Isoparaffin | 0.40 |
| Butylene Glycol | 0.16 |
| Glycerol | 0.16 |
| Cetearyl Alcohol | 0.10 |
| Cetyl Palmitate | 0.10 |
| Cocoglycerides | 0.10 |
| Laureth-7 | 0.10 |
| 4,5,7-Trihydroxyisoflavone | 0.01 to 10 |
| Extract of *Enteromorpha compressa* | 0.01 to 5 |
| *Lentinus edodes* | 0.02 to 5 |
| Extract of flowers of *Sophora japonica* | 0.01 to 20 |
| Extract of *Centella asiatica* | 0.01 to 5 |
| Hydrolysed soya protein | 0.01 to 10 |
| Preservative system | QS |
| Perfume | QS |

Example 11

Formulation of a Spray (Expressed in %)

| | |
|---|---|
| Water | Q.S. 100 |
| Glycerol | 4.00 |
| Montmorillonite | 3.00 |
| PEG-6 | 3.00 |
| Glycine | 0.30 |
| Citric acid | 0.09 |
| 4,5,7-Trihydroxyisoflavone | 0.01 to 10 |

-continued

| | |
|---|---|
| Extract of *Enteromorpha compressa* | 0.01 to 5 |
| Extract of flowers of *Sophora japonica* | 0.01 to 20 |
| Extract of *Centella asiatica* | 0.01 to 5 |
| Hydrolysed soya protein | 0.01 to 10 |
| Preservative system | QS |
| Perfume | QS |

What is claimed is:

1. A method of inhibiting development of cellulite and subcutaneous accumulations of fat in a subject having cellulite or subcutaneous accumulations of fat comprising administering to the subject an effective amount of a pharmaceutical composition comprising a polysaccharide extract derived from an aqueous extract and alcohol precipitate of fungus of the genus *Lentinus* comprising monosaccharides, polysaccharides and, by weight, from 2 to 8% of trehalose, from 1 to 4% of glucose and from 30 to 60% of alditols relative to the total weight of the dry extract, wherein the development of cellulite and subcutaneous accumulations of fat is inhibited, and wherein the pharmaceutical composition is administered to at least one of a hip, thigh, buttock, knee, and arm.

2. The method of claim 1, wherein the administration is topical.

3. The method of claim 1, wherein the polysaccharide extract is further defined as comprising, by weight, from 2 to 6% of trehalose, from 2 to 3% of glucose and from 45 to 55% of alditols relative to the total weight of the dry extract.

4. The method of claim 1, wherein the polysaccharide extract is further defined as comprising, by weight, from 3 to 5% of trehalose, from 2 to 3% of glucose and from 45 to 50% of alditols relative to the total weight of the dry extract.

5. The method of claim 1, wherein the alditols comprise arabinitol and mannitol.

6. The method of claim 1, wherein the polysaccharide extract is further defined as derived from the mushroom *Lentinus edodes*.

7. The method of claim 1, wherein the polysaccharide extract is further defined by the mass spectrometry analyses in FIGS. 1 and 2.

8. The method of claim 1, wherein the pharmaceutical composition is adapted for topical administration.

9. The method of claim 1, wherein expression of sirtuin protein is activated.

10. The method of claim 9, wherein the sirtuin protein is SIRT-1.

* * * * *